United States Patent [19]

Norman

[11] Patent Number: 5,628,971
[45] Date of Patent: May 13, 1997

[54] APPARATUS FOR STORING AND STERILIZING OBJECTS

[76] Inventor: Geraldine U. Norman, 4018-D Bannockburn Pl., Charlotte, N.C. 28211

[21] Appl. No.: 373,630

[22] Filed: Jan. 17, 1995

[51] Int. Cl.[6] ............................................. A61L 9/00
[52] U.S. Cl. ................... 422/301; 134/56 R; 134/58 R; 134/113; 134/135; 134/137; 134/140; 134/164; 134/165; 422/28; 422/105; 422/116; 422/292; 422/300
[58] Field of Search ...................................... 422/292, 300, 422/301, 28, 905, 116, 105; 134/56 R, 58 R, 113, 135, 137, 140, 164, 165

[56] References Cited

U.S. PATENT DOCUMENTS

| | | | |
|---|---|---|---|
| 816,886 | 4/1906 | Shonnard | 422/301 |
| 929,307 | 7/1909 | Holden | 422/301 |
| 1,193,129 | 8/1916 | Dorough | 422/301 |
| 1,485,797 | 3/1924 | Merseles | 422/301 X |
| 1,767,034 | 6/1930 | Andresen | 422/301 |
| 1,979,241 | 11/1934 | Albanese et al. | 422/300 X |
| 2,095,154 | 10/1937 | Scott | 422/300 |
| 2,499,891 | 3/1950 | Wagner | 422/301 |
| 3,292,993 | 12/1966 | Musso | 422/300 |
| 3,365,267 | 1/1968 | McKiney et al. | 422/300 X |
| 3,419,346 | 12/1968 | Nicholas | 422/116 |
| 3,460,899 | 8/1969 | Miller | 422/300 |
| 3,759,594 | 9/1973 | Cobb | 312/31 |
| 3,955,922 | 5/1976 | Moulthrop | 21/102 R |
| 3,966,408 | 6/1976 | Drennen et al. | 422/301 |
| 4,327,060 | 4/1982 | Nisii | 422/300 |
| 4,448,750 | 5/1984 | Fuesting | 422/20 |
| 4,746,496 | 5/1988 | Sorochenko et al. | 422/292 |
| 4,816,232 | 3/1989 | Barrau et al. | 422/301 |
| 4,973,847 | 11/1990 | Lackey et al. | 250/455.1 |
| 5,185,532 | 2/1993 | Zabsky et al. | 250/455.11 |
| 5,225,172 | 7/1993 | Meyler et al. | 422/300 |

Primary Examiner—Robert J. Warden
Assistant Examiner—Krisanne M. Thornton
Attorney, Agent, or Firm—W. Thad Adams, III, P.A.

[57] ABSTRACT

An apparatus and method for storing and sterilizing objects is provided. The apparatus includes a housing, and a tray supported within the housing for storing the objects to be sterilized. A sterilizing solution is located within the housing and below the tray. An elevator assembly lowers the tray downwardly to immerse the objects in the sterilizing solution, and lifts the tray upwardly to remove the objects from the sterilizing solution for further storage until use.

5 Claims, 3 Drawing Sheets

APPARATUS FOR STORING AND STERILIZING OBJECTS

TECHNICAL FIELD AND BACKGROUND OF THE INVENTION

This invention relates to an apparatus and method for storing and sterilizing objects, such as haircutting shears. In alternative applications, the invention may be used for sterilizing hair combs, manicure tools, dental or medical instruments, and other related devices. Although haircutting shears are not commonly sterilized after each use, California has recently enacted a law requiring such sterilization. Other states have not presently followed suit, but are expected to shortly.

According to the prior art, haircutting shears are commonly sterilized by submerging the shears in a sterilizing solution until needed by a user. Since each pair of used shears must be periodically sterilized, two or more shears are generally stored in the solution at any one time. If the shears are soiled by being dropped onto the floor or by cutting the stylist or customer during service, the stylist can readily obtain a second pair of shears and continue cutting while the soiled pair is being sterilized.

Depending upon the work load of the user and the attentiveness of the user to sterilization, any given pair of shears may remain in the sterilizing solution for an inadequate amount of time for sterilization to occur, or for hours without use. Because of this, the shears are either non-sterile or prone to corrosion and rust.

The present invention addresses this and other problems of sterilizing haircutting shears by providing an apparatus which stores several pairs of shears, dips the blades of the shears in a sterilizing solution for a predetermined length of time sufficient to achieve sterilization, such as 10 or 15 minutes, and then automatically removes the shears from the solution for continued storage until use. The invention ensures proper and sufficient sterilization of the shears without corrosion and rusting. Moreover, the invention allows convenient access to one or more pairs of sterilized shears at any given time.

SUMMARY OF THE INVENTION

Therefore, it is an object of the invention to provide an apparatus for sterilizing objects, such as haircutting shears.

It is another object of the invention to provide an apparatus which stores several pairs of non-sterile shears, and automatically dips the blades of the shears in a sterilizing solution for a predetermined length of time.

It is another object of the invention to provide an apparatus which automatically removes the shears from the sterilizing solution after the shears have been sufficiently sterilized.

It is another object of the invention to provide an apparatus which indicates to a user the precise length of time in which the shears have been immersed in the sterilizing solution.

These and other objects of the present invention are achieved in the preferred embodiments disclosed below by providing an apparatus for storing and sterilizing objects. The apparatus includes a housing, and carrier means supported within the housing for storing the objects to be sterilized. A sterilizing solution is located within the housing and below the carrier means. Elevator means lowers the carrier means downwardly to immerse the objects in the sterilizing solution, and lifts the carrier means upwardly to remove the objects from the sterilizing solution for further storage until use.

According to one preferred embodiment of the invention, the elevator means includes a lift cable and an actuating arm. The lift cable is connected at one end thereof to the carrier means and at the opposite end thereof to the actuating arm. The actuating arm is movable between a first position and a second position for lifting and lowering the carrier means.

According to another preferred embodiment of the invention, the elevator means further includes an electric motor for moving the actuating arm between the first and second positions.

According to yet another preferred embodiment of the invention, a timer means is electrically connected to the motor. The timer means activates the motor to move the actuating arm between the first position and the second position according to a preset interval, thereby immersing the objects in the sterilizing solution for a preset time period.

According to yet another preferred embodiment of the invention, a return spring is connected at one end thereof to a base of the housing and at an opposite end thereof to the carrier means. The return spring normally urges the carrier means downwardly, and supplies tension to the lift cable.

According to yet another preferred embodiment of the invention, the carrier means is a removable tray supported within the housing.

According to yet another preferred embodiment of the invention, the removable tray includes a plurality of holes therein for storing the objects to be sterilized, and for locating a portion of the objects below the tray for immersion in the sterilizing solution.

According to yet another preferred embodiment of the invention, spaced apart support shelves are provided for supporting the tray within the housing.

According to yet another preferred embodiment of the invention, the support shelves are located on vertical guide rods for guiding the shelves and tray as the tray moves vertically within the housing.

According to yet another preferred embodiment of the invention, a time display means is provided for indicating to a user the amount of time in which the objects have been immersed in the sterilizing solution.

According to one preferred embodiment of the invention, an apparatus for storing and sterilizing shears includes a housing, and a tray supported within the housing. The tray defines a plurality of holes therein for storing the shears to be sterilized. A sterilizing solution is located within the housing and below the tray. Elevator means lowers the tray downwardly from a shear storage position to a shear immersing position, and lifts the tray upwardly from the shear immersing position back to the shear storage position. Timer means cooperates with the elevator means for lifting the tray upwardly from the shear immersing position to the shear storage position after a preset time period.

An embodiment of the method according to the invention comprises the steps of storing a plurality of objects on carrier means. The objects to be sterilized are immersed in a sterilizing solution, and automatically removed from the sterilizing solution after a preset time period for further storage until use.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
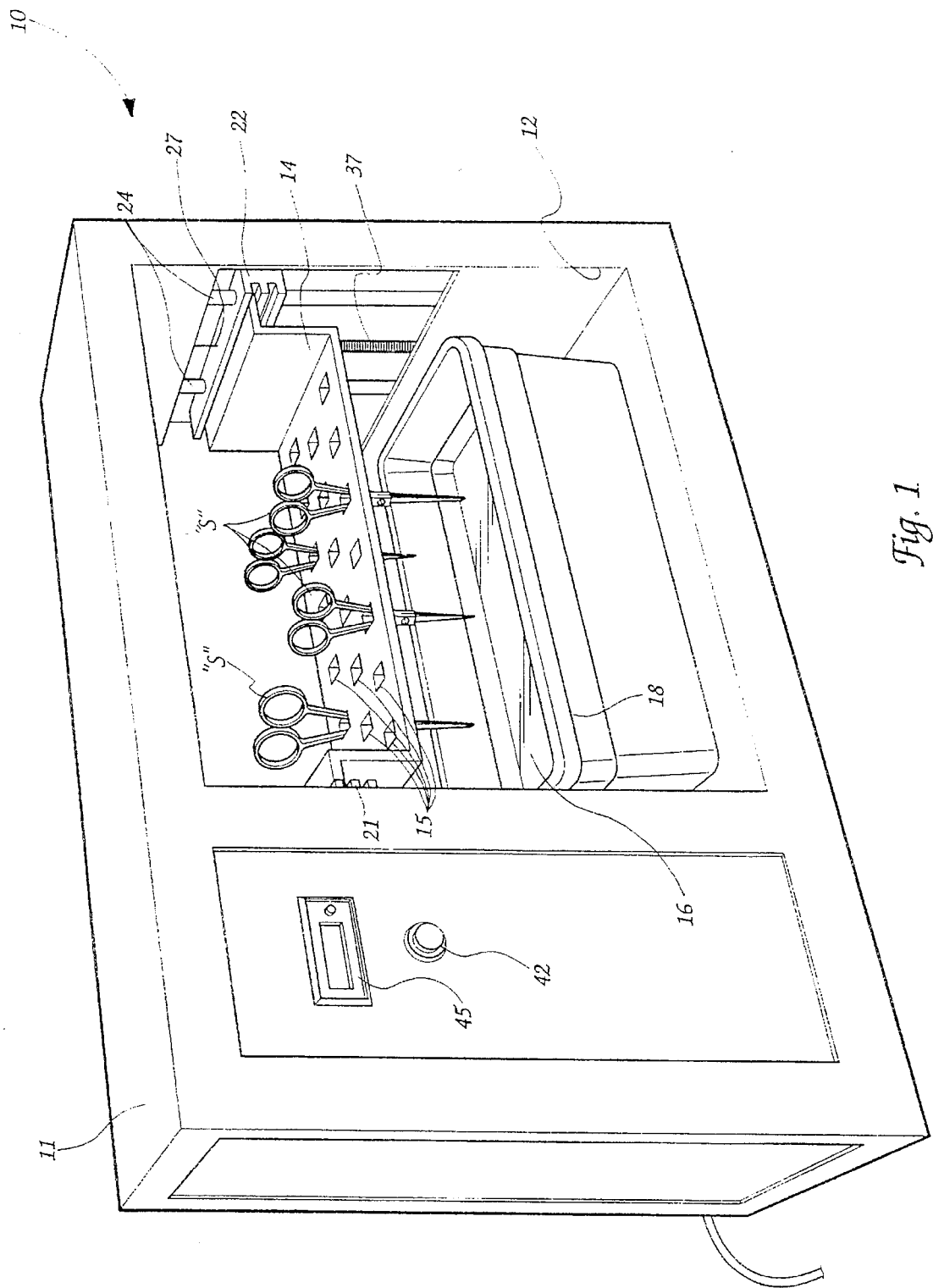
FIG. 1 is a perspective view of an apparatus for sterilizing objects according to one preferred embodiment of the invention.

Referring now specifically to the drawings, an apparatus for sterilizing objects according to the present invention is illustrated in FIG. 1 and shown generally at reference numeral 10. The apparatus 10 is especially applicable for storing and sterilizing haircutting shears "S". In alternative applications, the apparatus 10 with a tray particularly suited to the article may be used for sterilizing hair combs, manicure tools, dental or medical instruments, and other such devices (not shown).

The apparatus 10 includes a housing 11 with a user access opening 12, and a removable tray 14 located in the access opening 12 for carrying the shears "S" to be sterilized. The tray 14 preferably includes several holes 15 for receiving and storing the shears "S", and for locating the blades of the shears "S" beneath the tray 14 for immersion in a sterilizing solution 16. The holes 15 are sufficiently large to permit the blades of the shears "S" to be fully opened when being sterilized.

The sterilizing solution 16 is contained in a pan 18 positioned directly below the tray 14. The sterilizing solution 16 may be any suitable known solution.

Figure 2:
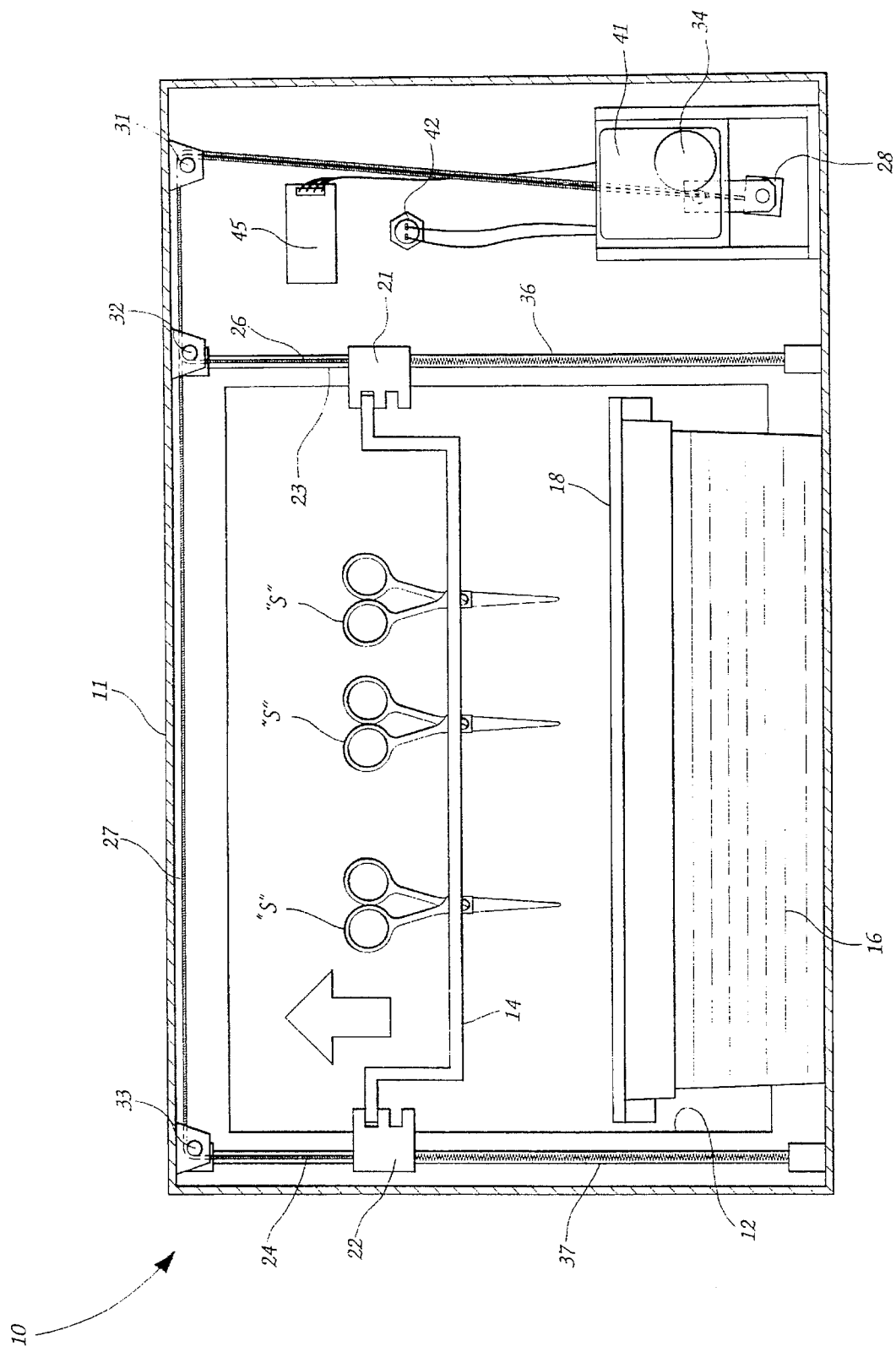
FIG. 2 is a rear elevational view of the apparatus with a back wall of the housing removed to illustrate the elevator means, and showing the support tray in the raised position.
Figure 3:
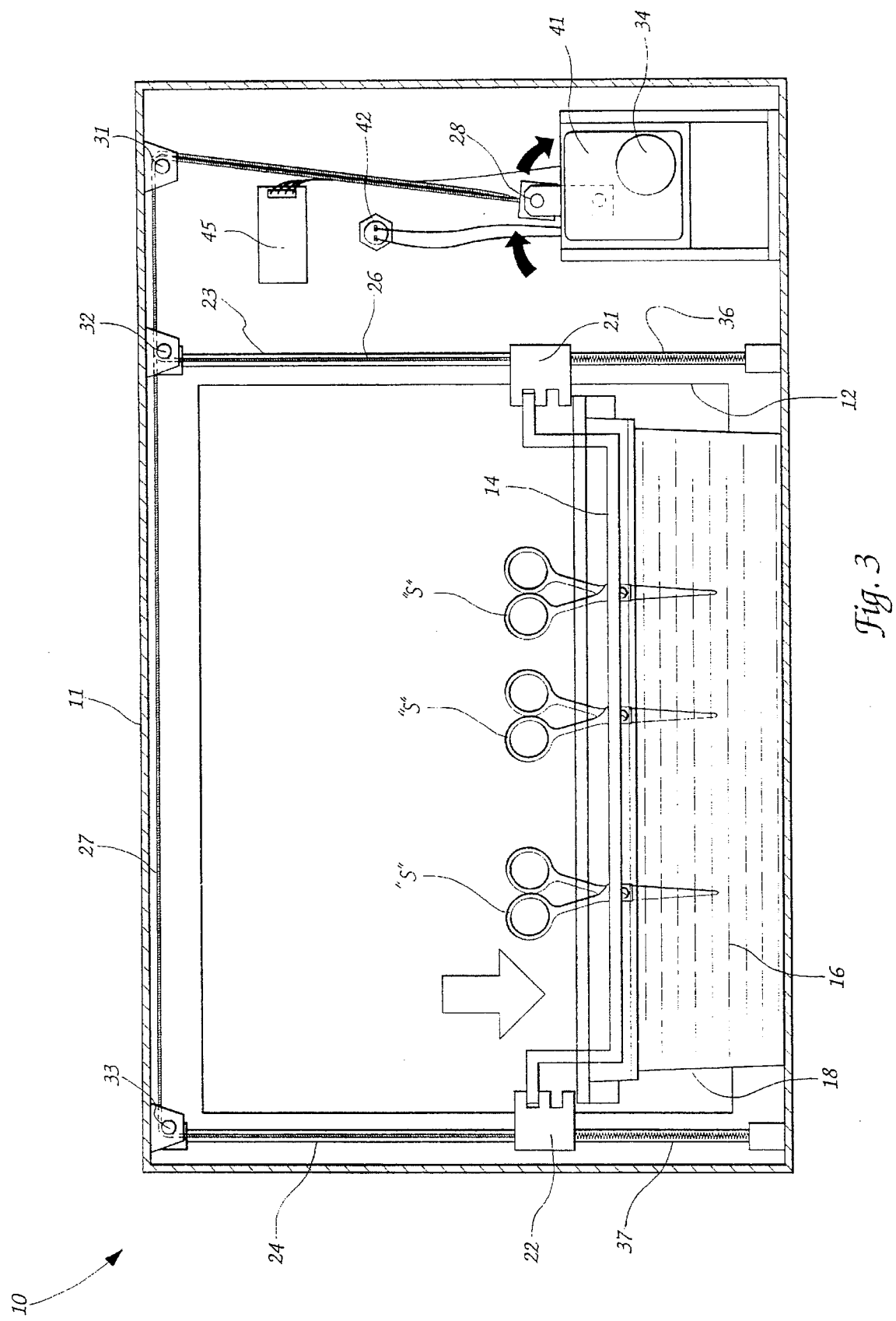
FIG. 3 is a rear elevational view of the apparatus with a back wall of the housing removed to illustrate the elevator means, and showing the support tray in the lowered position with the blades of the shears immersed in the sterilizing solution.

As best shown in FIGS. 2 and 3, the tray 14 is supported within the access opening 12 by spaced-apart support shelves 21 and 22. The support shelves 21 and 22 are located on respective pairs of guide rods 23 and 24, and move vertically along the guide rods 23 and 24 by elevator means described below for lifting and lowering the tray 14. In addition, a clear plastic door (not shown) may be pivotably attached to the housing 11 at the access opening 12 for being opened and closed by the user.

The elevator means includes first and second lift cables 26 and 27 connected to an actuating arm 28 and the support shelves 21 and 22, respectively. The first lift cable 26 extends from the actuating arm 28 over pulleys 31 and 32 to the support shelf 21. The second lift cable 27 extends from the actuating arm 28 over pulleys 31, 32, and 33 to the opposite support shelf 22.

An electric motor 34 rotates the actuating arm 28 in a circular path between a vertically down position and a vertically up position. When the arm 28 is in the down position, the cables 26 and 27 locate the support shelves 21 and 22 and tray 14 near an upper end of the guide rods 23 and 24 with the blades of the shears "S" completely above the sterilizing solution 16, as shown in FIG. 2. When the arm 28 rotates to the up position as shown in FIG. 3, the support shelves 21 and 22 and tray 14 are moved downwardly by the cables 26 and 27 to immerse the blades of the shears "S" in the sterilizing solution 16. Preferably, springs 36 and 37 are connected to the support shelves 21 and 22 and to the base of the housing 11 for normally urging the support shelves 21 and 22 downwardly, and for supplying tension to the cables 26 and 27.

A timer 41 is electrically connected to the motor 34, and to a push button control 42 located on the front side of the housing 11 (See FIG. 1). When depressed, the push button control 42 closes an electric contact which simultaneously triggers a first relay coil and a second delay-on relay coil. The first relay coil controls operation of the motor, and causes a 180 degree rotation of the actuating arm 28 from the down position shown in FIG. 2 to the up position shown in FIG. 3. A limit switch (not shown) or other suitable means stops the rotational movement of the arm 28 after reaching the vertically up position. As shown in FIG. 3, the blades of the shears "S" are completely submerged in the sterilizing solution 16.

After a preset length of time, such as 10 or 15 minutes, the delay-on relay coil activates and restarts the motor 34. The motor 34 causes a second 180 degree rotation of the actuating arm 28 to return the actuating arm 28 from the up position to the down position shown in FIG. 2. A second limit switch (not shown) or other suitable means stops the rotational movement of the arm 28 after reaching the vertically down position. The blades of the shears "S" are now sufficiently sterilized and completely removed from the sterilizing solution 16 for further storage until use. Excess solution drips from the shears "S" back into the pan 18.

The timer 41 may include any other desired electrical circuitry for triggering operation of the motor 34 at a preset time interval. Operation of such timers are generally known and understood by those of ordinary skill in the art.

In addition, a time display device 45 is preferably located on the front wall of the housing 11 for indicating to the user the exact time in which the shears "S" have been immersed in the sterilizing solution 16. The time display device 45 includes manual start, stop, and reset buttons, and operates like a conventional stop watch.

An apparatus and method of sterilizing objects is described above. Various details of the invention may be changed without departing from its scope. Furthermore, the foregoing description of the preferred embodiment of the invention is provided for the purpose of illustration only and not for the purpose of limitation—the invention being defined by the claims.

I claim:

1. An apparatus for storing and sterilizing a plurality of hair-cutting shears each having a handle for being gripped by a user and blades for cutting, said apparatus comprising:
   (a) a housing;
   (b) a sterilizing solution contained in a pan in said housing;
   (c) a tray supported within said housing on first and second spaced support shelves and being vertically movable between a shear storing position where the shears reside entirely above the sterilizing solution and shear sterilizing position where the blades are immersed in the sterilizing solution, said tray having a plurality of holes therein for receiving respective blades of said shears therethrough, and supporting the shears in a substantially upright condition with the blades extending vertically downwardly through the holes on a bottom side of said tray, and the handles engaging said tray at respective holes and extending vertically upwardly from the holes on a top side of said tray;
   (d) elevator means for lowering said tray downwardly from the shear storing position to the shear sterilizing position, and for returning said tray from the shear sterilizing position to the shear storing position, said elevator means comprising a pair of lift cables and an actuating arm, the lift cables interconnecting the first and second support shelves and the actuating arm, and the actuating arm being movable in a lifting direction and a lowering direction for lifting and lowering the support shelves to move the shears out of and into the sterilizing solution; and (e) first and second return springs connected under tension at respective opposing ends thereof to a base of the housing and to the first and second support shelves for urging the first and second support shelves downwardly and supplying tension to the lift cables.

2. An apparatus according to claim 1, wherein said first and second support shelves are located on vertical guide rods for guiding the shelves and tray as the tray moves vertically within the housing.

3. An apparatus according to claim 1, wherein said elevator means further comprises an electric motor connected to said actuating arm for moving said actuating arm in the lifting and lowering directions.

4. An apparatus according to claim 3, and including a motor-activating timer electrically connected to said motor and activating said motor according to a preset interval to automatically move the actuating arm in the lifting and lowering directions, whereby the blades of the shears remain immersed in the sterilizing solution for a preset time period.

5. An apparatus according to claim 4, and including a time display for indicating to a user the amount of time in which the blades of the shears are immersed in the sterilizing solution.

* * * * *